US008017142B2

(12) United States Patent
Claude et al.

(10) Patent No.: US 8,017,142 B2
(45) Date of Patent: Sep. 13, 2011

(54) POLYSULFONE BLOCK COPOLYMERS AS DRUG-ELUTING COATING MATERIAL

(75) Inventors: Charles D. Claude, San Jose, CA (US); Ni Ding, San Jose, CA (US); Yeung Siu Yu, Pleasanton, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 190 days.

(21) Appl. No.: 12/476,987

(22) Filed: Jun. 2, 2009

(65) Prior Publication Data

US 2009/0238856 A1 Sep. 24, 2009

Related U.S. Application Data

(62) Division of application No. 10/723,137, filed on Nov. 25, 2003, now Pat. No. 7,560,492.

(51) Int. Cl.
*A61F 2/00* (2006.01)
*A61K 47/00* (2006.01)
*A61K 47/30* (2006.01)

(52) U.S. Cl. ..... 424/423; 424/422; 514/772; 514/772.1; 514/772.3

(58) Field of Classification Search .................. 424/423, 424/422; 514/772.1, 772, 772.3
See application file for complete search history.

(56) References Cited

U.S. PATENT DOCUMENTS

| | | | |
|---|---|---|---|
| 4,329,383 A | 5/1982 | Joh | |
| 4,733,665 A | 3/1988 | Palmaz | |
| 4,800,882 A | 1/1989 | Gianturco | |
| 4,882,168 A | 11/1989 | Casey et al. | |
| 4,886,062 A | 12/1989 | Wiktor | |
| 4,941,870 A | 7/1990 | Okada et al. | |
| 4,977,901 A | 12/1990 | Ofstead | |
| 5,112,457 A | 5/1992 | Marchant | |
| 5,165,919 A | 11/1992 | Sasaki et al. | |
| 5,221,724 A | 6/1993 | Li et al. | |
| 5,272,012 A | 12/1993 | Opolski | |
| 5,292,516 A | 3/1994 | Viegas et al. | |
| 5,298,260 A | 3/1994 | Viegas et al. | |
| 5,300,295 A | 4/1994 | Viegas et al. | |
| 5,306,501 A | 4/1994 | Viegas et al. | |
| 5,328,471 A | 7/1994 | Slepian | |
| 5,330,768 A | 7/1994 | Park et al. | |
| 5,380,299 A | 1/1995 | Fearnot et al. | |
| 5,417,981 A | 5/1995 | Endo et al. | |
| 5,447,724 A | 9/1995 | Helmus et al. | |
| 5,455,040 A | 10/1995 | Marchant | |
| 5,462,990 A | 10/1995 | Hubbell et al. | |
| 5,464,650 A | 11/1995 | Berg et al. | |
| 5,569,463 A | 10/1996 | Helmus et al. | |
| 5,578,073 A | 11/1996 | Haimovich et al. | |
| 5,605,696 A | 2/1997 | Eury et al. | |
| 5,609,629 A | 3/1997 | Fearnot et al. | |
| 5,624,411 A | 4/1997 | Tuch | |
| 5,628,730 A | 5/1997 | Shapland et al. | |
| 5,649,977 A | 7/1997 | Campbell | |
| 5,658,995 A | 8/1997 | Kohn et al. | |
| 5,667,767 A | 9/1997 | Greff et al. | |
| 5,670,558 A | 9/1997 | Onishi et al. | |
| 5,679,400 A | 10/1997 | Tuch | |
| 5,700,286 A | 12/1997 | Tartaglia et al. | |
| 5,702,754 A | 12/1997 | Zhong | |
| 5,716,981 A | 2/1998 | Hunter et al. | |
| 5,735,897 A | 4/1998 | Buirge | |
| 5,746,998 A | 5/1998 | Torchilin et al. | |
| 5,776,184 A | 7/1998 | Tuch | |
| 5,788,979 A | 8/1998 | Alt et al. | |
| 5,800,392 A | 9/1998 | Racchini | |
| 5,820,917 A | 10/1998 | Tuch | |
| 5,824,048 A | 10/1998 | Tuch | |
| 5,824,049 A | 10/1998 | Ragheb et al. | |
| 5,830,178 A | 11/1998 | Jones et al. | |
| 5,837,008 A | 11/1998 | Berg et al. | |
| 5,837,313 A | 11/1998 | Ding et al. | |
| 5,851,508 A | 12/1998 | Greff et al. | |
| 5,858,746 A | 1/1999 | Hubbell et al. | |
| 5,865,814 A | 2/1999 | Tuch | |
| 5,869,127 A | 2/1999 | Zhong | |
| 5,873,904 A | 2/1999 | Ragheb et al. | |
| 5,876,433 A | 3/1999 | Lunn | |
| 5,877,224 A | 3/1999 | Brocchini et al. | |
| 5,925,720 A | 7/1999 | Kataoka et al. | |
| 5,955,509 A | 9/1999 | Webber et al. | |
| 5,971,954 A | 10/1999 | Conway et al. | |
| 5,980,928 A | 11/1999 | Terry | |
| 5,980,972 A | 11/1999 | Ding | |

(Continued)

FOREIGN PATENT DOCUMENTS

EP 0 301 856 2/1989

(Continued)

OTHER PUBLICATIONS

Anonymous, *Cardiologists Draw—Up the Dream Stent*, Clinica 710:15 (Jun. 17, 1996), http://www.dialogweb.com/cgi/document?reg=1061848202959, printed Aug. 25, 2003 (2 pages).

Anonymous, *Heparin-coated stents cut complications by 30%*, Clinica 732:17 (Nov. 18, 1996), http://www.dialogweb.com/cgi/document?reg=1061847871753, printed Aug. 25, 2003 (2 pages).

Anonymous, *Rolling Therapeutic Agent Loading Device for Therapeutic Agent Delivery or Coated Stent* (Abstract 434009), Res. Disclos. pp. 974-975 (Jun. 2000).

Anonymous, *Stenting continues to dominate cardiology*, Clinica 720:22 (Sep. 2, 1996), http://www.dialogweb.com/cgi/document?reg=1061848017752, printed Aug. 25, 2003 (2 pages).

Aoyagi et al., *Preparation of cross-linked aliphatic polyester and application to thertmo-responsive material*, Journal of Controlled Release 32:87-96 (1994).

Barath et al., *Low Dose of Antitumor Agents Prevents Smooth Muscle Cell Proliferation After Endothelial Injury*, JACC 13(2): 252A (Abstract) (Feb. 1989).

Barbucci et al., *Coating of commercially available materials with a new heparinizable material*, J. Biomed. Mater. Res. 25:1259-1274 (Oct. 1991).

(Continued)

*Primary Examiner* — Gina C Yu
*Assistant Examiner* — Michael B Pallay
(74) *Attorney, Agent, or Firm* — Squire, Sanders & Dempsey (US) LLP

(57) ABSTRACT

A polymeric composition comprising a polysulfone polymer and an elastomeric polymer for use as a coating composition for coating an implantable device, such as a DES, and methods of making and using the implantable device are provided.

9 Claims, No Drawings

U.S. PATENT DOCUMENTS

| | | |
|---|---|---|
| 5,997,517 A | 12/1999 | Whitbourne |
| 6,010,530 A | 1/2000 | Goicoechea |
| 6,013,099 A | 1/2000 | Dinh et al. |
| 6,015,541 A | 1/2000 | Greff et al. |
| 6,033,582 A | 3/2000 | Lee et al. |
| 6,042,875 A | 3/2000 | Ding et al. |
| 6,051,576 A | 4/2000 | Ashton et al. |
| 6,051,648 A | 4/2000 | Rhee et al. |
| 6,056,993 A | 5/2000 | Leidner et al. |
| 6,060,451 A | 5/2000 | DiMaio et al. |
| 6,060,518 A | 5/2000 | Kabanov et al. |
| 6,080,488 A | 6/2000 | Hostettler et al. |
| 6,096,070 A | 8/2000 | Ragheb et al. |
| 6,099,562 A | 8/2000 | Ding et al. |
| 6,110,188 A | 8/2000 | Narciso, Jr. |
| 6,110,483 A | 8/2000 | Whitbourne et al. |
| 6,113,629 A | 9/2000 | Ken |
| 6,120,536 A | 9/2000 | Ding et al. |
| 6,120,904 A | 9/2000 | Hostettler et al. |
| 6,121,027 A | 9/2000 | Clapper et al. |
| 6,129,761 A | 10/2000 | Hubbell |
| 6,153,252 A | 11/2000 | Hossainy et al. |
| 6,165,212 A | 12/2000 | Dereume et al. |
| 6,203,551 B1 | 3/2001 | Wu |
| 6,231,600 B1 | 5/2001 | Zhong |
| 6,240,616 B1 | 6/2001 | Yan |
| 6,245,753 B1 | 6/2001 | Byun et al. |
| 6,251,136 B1 | 6/2001 | Guruwaiya et al. |
| 6,254,632 B1 | 7/2001 | Wu et al. |
| 6,258,121 B1 | 7/2001 | Yang et al. |
| 6,283,947 B1 | 9/2001 | Mirzaee |
| 6,283,949 B1 | 9/2001 | Roorda |
| 6,284,305 B1 | 9/2001 | Ding et al. |
| 6,287,628 B1 | 9/2001 | Hossainy et al. |
| 6,299,604 B1 | 10/2001 | Ragheb et al. |
| 6,306,176 B1 | 10/2001 | Whitbourne |
| 6,331,313 B1 | 12/2001 | Wong et al. |
| 6,335,029 B1 | 1/2002 | Kamath et al. |
| 6,346,110 B2 | 2/2002 | Wu |
| 6,358,556 B1 | 3/2002 | Ding et al. |
| 6,379,381 B1 | 4/2002 | Hossainy et al. |
| 6,395,326 B1 | 5/2002 | Castro et al. |
| 6,419,692 B1 | 7/2002 | Yang et al. |
| 6,451,373 B1 | 9/2002 | Hossainy et al. |
| 6,494,862 B1 | 12/2002 | Ray et al. |
| 6,503,556 B2 | 1/2003 | Harish et al. |
| 6,503,954 B1 | 1/2003 | Bhat et al. |
| 6,506,437 B1 | 1/2003 | Harish et al. |
| 6,527,801 B1 | 3/2003 | Dutta |
| 6,527,863 B1 | 3/2003 | Pacetti et al. |
| 6,540,776 B2 | 4/2003 | Sanders Millare et al. |
| 6,544,223 B1 | 4/2003 | Kokish |
| 6,544,543 B1 | 4/2003 | Mandrusov et al. |
| 6,544,582 B1 | 4/2003 | Yoe |
| 6,555,157 B1 | 4/2003 | Hossainy |
| 6,558,733 B1 | 5/2003 | Hossainy et al. |
| 6,565,659 B1 | 5/2003 | Pacetti et al. |
| 6,572,644 B1 | 6/2003 | Moein |
| 6,585,765 B1 | 7/2003 | Hossainy et al. |
| 6,585,926 B1 | 7/2003 | Mirzaee |
| 6,605,154 B1 | 8/2003 | Villareal |
| 6,641,611 B2 | 11/2003 | Jayaraman |
| 6,712,845 B2 | 3/2004 | Hossainy |
| 6,759,054 B2 | 7/2004 | Chen et al. |
| 2002/0077693 A1 | 6/2002 | Barclay et al. |
| 2002/0091433 A1 | 7/2002 | Ding et al. |
| 2002/0155212 A1 | 10/2002 | Hossainy |
| 2003/0065377 A1 | 4/2003 | Davila et al. |
| 2003/0099712 A1 | 5/2003 | Jayaraman |
| 2005/0129731 A1 | 6/2005 | Horres et al. |

FOREIGN PATENT DOCUMENTS

| | | |
|---|---|---|
| EP | 0 514 406 | 11/1992 |
| EP | 0 604 022 | 6/1994 |
| EP | 0 623 354 | 11/1994 |
| EP | 0 665 023 | 8/1995 |
| EP | 0 701 802 | 3/1996 |
| EP | 0 716 836 | 6/1996 |
| EP | 0 809 999 | 12/1997 |
| EP | 0 832 655 | 4/1998 |
| EP | 0 850 651 | 7/1998 |
| EP | 0 879 595 | 11/1998 |
| EP | 0 910 584 | 4/1999 |
| EP | 0 923 953 | 6/1999 |
| EP | 0 953 320 | 11/1999 |
| EP | 0 970 711 | 1/2000 |
| EP | 0 982 041 | 3/2000 |
| EP | 1 273 314 | 1/2003 |
| JP | 2001-190687 | 7/2001 |
| WO | WO 91/12846 | 9/1991 |
| WO | WO 95/10989 | 4/1995 |
| WO | WO 96/40174 | 12/1996 |
| WO | WO 97/10011 | 3/1997 |
| WO | WO 97/45105 | 12/1997 |
| WO | WO 97/46590 | 12/1997 |
| WO | WO 98/17331 | 4/1998 |
| WO | WO 98/36784 | 8/1998 |
| WO | WO 99/01118 | 1/1999 |
| WO | WO 99/38546 | 8/1999 |
| WO | WO 99/63981 | 12/1999 |
| WO | WO 00/02599 | 1/2000 |
| WO | WO 00/12147 | 3/2000 |
| WO | WO 00/18446 | 4/2000 |
| WO | WO 00/64506 | 11/2000 |
| WO | WO 01/01890 | 1/2001 |
| WO | WO 01/15751 | 3/2001 |
| WO | WO 01/17577 | 3/2001 |
| WO | WO 01/45763 | 6/2001 |
| WO | WO 01/49338 | 7/2001 |
| WO | WO 01/74414 | 10/2001 |
| WO | WO 02/03890 | 1/2002 |
| WO | WO 02/26162 | 4/2002 |
| WO | WO 02/34311 | 5/2002 |
| WO | WO 02/056790 | 7/2002 |
| WO | WO 03/000308 | 1/2003 |
| WO | WO 03/022323 | 3/2003 |
| WO | WO 03/028780 | 4/2003 |
| WO | WO 03/037223 | 5/2003 |
| WO | WO 03/039612 | 5/2003 |

OTHER PUBLICATIONS

Chung et al., *Inner core segment design for drug delivery control of thermo-responsive polymeric micelles*, Journal of Controlled Release 65:93-103 (2000).

C&EN "Chemistry Grads Post Gians in 2005", (2006).

Dev et al., *Kinetics of Drug Delivery to the Arterial Wall Via Polyurethane-Coated Removable Nitinol Stent: Comparative Study of Two Drugs*, Catheterization and Cardiovascular Diagnosis 34:272-278 (1995).

Dichek et al., *Seeding of Intravascular Stents with Genetically Engineered Endothelial Cells*, Circ. 80(5):1347-1353 (Nov. 1989).

Eigler et al., *Local Arterial Wall Drug Delivery from a Polymer Coated Removable Metallic Stent: Kinetics, Distribution, and Bioactivity of Forskolin*, JACC, 4A (701-1), Abstract (Feb. 1994).

Helmus, *Overview of Biomedical Materials*, MRS Bulletin, pp. 33-38 (Sep. 1991).

Herdeg et al., *Antiproliferative Stent Coatings: Taxol and Related Compounds*, Semin. Intervent. Cardiol. 3:197-199 (1998).

Inoue et al., *An AB block copolymer of oligo(methyl methacrylate) and poly(acrylic acid) for micellar delivery of hydrophobic drugs*, Journal of Controlled Release 51:221-229 (1998).

Kataoka et al., *Block copolymer micelles as vehicles for drug delivery*, Journal of Controlled Release 24:119-132 (1993).

Levy et al., *Strategies for Treating Arterial Restenosis Using Polymeric Controlled Release Implants*, Biotechnol. Bioact. Polym. [Proc. Am. Chem. Soc. Symp.], pp. 259-268 (1994).

Liu et al., *Drug release characteristics of unimolecular polymeric micelles*, Journal of Controlled Release 68:167-174 (2000).

Marconi et al., *Covalent bonding of heparin to a vinyl copolymer for biomedical applications*, Biomaterials 18(12):885-890 (1997).

Matsumaru et al., *Embolic Materials For Endovascular Treatment of Cerebral Lesions*, J. Biomater. Sci. Polymer Edn 8(7):555-569 (1997).

Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull. 33(6) 2490-2498 (1985).

Miyazawa et al., *Effects of Pemirolast and Tranilast on Intimal Thickening After Arterial Injury in the Rat*, J. Cardiovasc. Pharmacol., pp. 157-162 (1997).

Nordrehaug et al., *A novel biocompatible coating applied to coronary stents*, EPO Heart Journal 14, p. 321 (P1694), Abstr. Suppl. (1993).

Ohsawa et al., *Preventive Effects of an Antiallergic Drug, Pemirolast Potassium, on Restenosis After Percutaneous Transluminal Coronary Angioplasty*, American Heart Journal 136(6):1081-1087 (Dec. 1998).

Ozaki et al., *New Stent Technologies*, Progress in Cardiovascular Diseases, Vol. XXXIX(2):129-140 (Sep./Oct. 1996).

Pechar et al., *Poly(ethylene glycol) Multiblock Copolymer as a Carrier of Anti-Cancer Drug Doxorubicin*, Bioconjucate Chemistry 11(2):131-139 (Mar./Apr. 2000).

Peng et al., *Role of polymers in improving the results of stenting in coronary arteries*, Biomaterials 17:685-694 (1996).

Shigeno, *Prevention of Cerebrovascular Spasm by Bosentan, Novel Endothelin Receptor*, Chemical Abstract 125:212307 (1996).

van Beusekom et al., *Coronary stent coatings*, Coronary Artery Disease 5(7):590-596 (Jul. 1994).

Wilensky et al., *Methods and Devices for Local Drug Delivery in Coronary and Peripheral Arteries*, Trends Cardiovasc. Med. 3(5):163-170 (1993).

Yokoyama et al., *Characterization of physical entrapment and chemical conjugation of adriamycin in polymeric micelles and their design for in vivo delivery to a solid tumor*, Journal of Controlled Release 50:79-92 (1998).

POLYSULFONE BLOCK COPOLYMERS AS DRUG-ELUTING COATING MATERIAL

CROSS-REFERENCE TO RELATED APPLICATION

This application is a divisional application of U.S. application Ser. No. 10/723,137, filed on Nov. 25, 2003 now U.S. Pat. No. 7,560,492, the teaching of which is incorporated herein by reference in its entirety.

BACKGROUND OF THE INVENTION

1. Field of the Invention

This invention generally relates to a polysulfone composition useful for coating an implantable device such as a drug eluting stent.

2. Description of the Background

Blood vessel occlusions are commonly treated by mechanically enhancing blood flow in the affected vessels, such as by employing a stent. Stents are used not only for mechanical intervention but also as vehicles for providing biological therapy. To effect a controlled delivery of an active agent in stent medication, the stent can be coated with a biocompatible polymeric coating. The biocompatible polymeric coating can function either as a permeable layer or a carrier to allow a controlled delivery of the agent.

Polymeric coatings for delivery of therapeutic agents on implantable devices, e.g., drug-eluting stents, often suffer from poor mechanical properties, poor surface properties and poor biocompatibility. A coating on a stent with such shortcomings would be unsatisfactory for use in a patient. For example, a stent with poor biocompatibility may illicit undesirable immuno reactions from the patient, and a stent with poor surface properties may not be effective in controlling release rate of an agent in the coating. Therefore, there is a need for polymeric coating compositions that provide coatings with balanced mechanical properties, optimal permeability and good biocompatibility.

The polymer and methods of making the polymer disclosed herein address the above described problems and needs.

SUMMARY OF THE INVENTION

Disclosed herein are a polymeric composition and a coating formed therefrom comprising an elastomeric polymer, a polysulfone polymer, and optionally a bioactive agent. The elastomeric polymer can be any polymer which is elastomeric and biostable. In one embodiment, the elastomeric polymer can be, for example, polyacrylate or polymethacrylate with long side chains such as poly(butyl methacrylate) or poly (lauryl methacrylate), polyisobutylene, polyhexafluoropentene, or polysiloxane. Representative long side chains include any side chains having at least two or more carbon atoms such ethyl, propyl, isopropyl, butyl, isobutyl, lauryl, hexyl, etc.

The polysulfone polymer and the elastomeric polymer can form a simple blend or a conjugate. The conjugate can be formed by a direct chemical bonding, hydrogen bonding, or ionic bonding. The conjugate can be, for example, an ionic pair or a block copolymer. In one embodiment, the conjugate has one of the following structures:

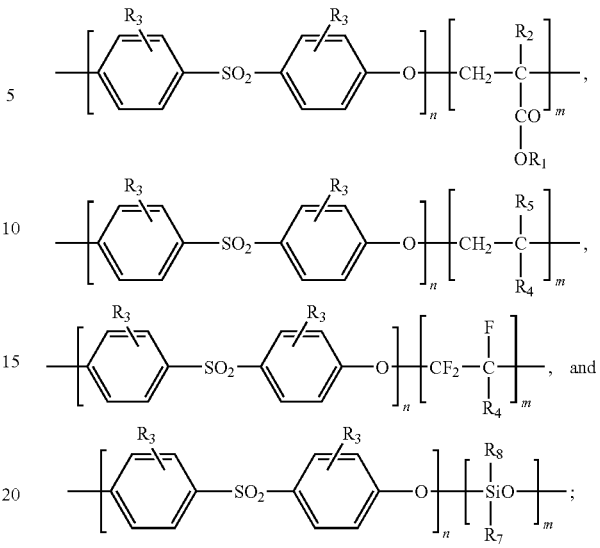

wherein $R_1$ is C1 to C10 alkyl, C2, C4 and C6 hydroxyalkyl, C1 to C6 fluoroalkyl, phenyl, substituted phenyl, polyethylene glycol, and polyalkylene oxide such as ethylene oxide or propylene oxide;

wherein $R_2$, $R_4$, $R_5$, $R_7$ and $R_8$ are independently hydrogen, C1 to C6 alkyl, C2, C4 and C6 hydroxyalkyl, C1 to C6 fluoroalkyl, phenyl, substituted phenyl, carboxyl, amido, or ester groups bearing a polyethylene glycol, and polyalkylene oxide;

wherein $R_3$ is hydrogen, alkyl, cycloalkyl, phenyl, carboxyl, halo, amino, hydroxyl, amido, sulfido, and polyalkylene oxide;

wherein $R_6$ is a perfluoroalkyl group; and wherein n and m are independently positive integers.

The coating composition thus formed can be coated onto an implantable device such as a drug-eluting stent (DES). The release rate of the bioactive agent on the implantable device can be controlled by varying the ratio of the polysulfone polymer over the elastomeric polymer, e.g., varying the n/m ratio of the copolymer described above.

DETAILED DESCRIPTION

Polysulfone Compositions

Disclosed herein are a polymeric composition comprising an elastomeric polymer, a polysulfone polymer, and optionally a bioactive agent. The composition can form a coating on an implantable device such as a DES. The implantable device thus formed can be used for treating a disorder in an animal such as a human being.

The polysulfone polymer and the elastomeric polymer can be present in the present application in any ratio, for example, a ratio of between about 99.5:0.5 and 0.5:99.5, between about 99:1 and 1:99, between about 95:5 and 5:95, between about 90:10 and 10:90, between about 80:20 and 20:80, between about 75:25 and 25:75, between about 70:30 and 30:70, between about 60:40 and 40:60, or about 50:50. The polysulfone polymer and the elastomeric polymer can be present in the form of polymer blends or conjugates.

As used herein, the term "conjugate" refers to a group of at least two materials, e.g., two molecules of different polymers, associated with each other in the form of an interaction such as ionic interaction, direct chemical bonding, hydrogen bonding, or van der Waals interaction. Exemplary conjugates include, but are not limited to, ion pairs, block copolymers such as one comprising a block of a polysulfone polymer and another block of an elastomeric polymer such as poly(butyl methacrylate) or poly(lauryl methacrylate).

Polysulfone Polymers

Polysulfone surfaces have long been known to be protein and cell resistant. The material has been used in several medical applications. Among them are kidney dialysis membranes and blood oxygenator membranes. Polysulfone polymers can be generated in laboratories via routine laboratory operations or commercially available. For example, there are two types of commercially available polysulfone polymers, one is one polyethersulfone, and the other was derivatized from bisphenol.

Elastomeric Polymers

The elastomeric polymers useful for forming the blend or conjugate with the polysulfone polymer described herein can be any biocompatible elastomeric polymers. Representative examples of such elastomeric polymers include, but not limited to, natural rubber, polyisobutylene, nylon, polysiloxanes, polyperfluoroalkylene such as polyhexafluoropropylene, polymers and copolymers of acrylates or methacrylates with long side chains such as poly(butyl methacrylate), poly(lauryl methacrylate), and polyalkylene oxide or polyalkylene oxide acrylates. In one embodiment, the blend or conjugate can exclude any of the aforementioned elastomeric polymers.

Conjugates

In accordance with one aspect of the invention, the conjugates disclosed herein can be ion pairs or can be conjugates having other ionic interaction, hydrogen bonding, or van der Waals interaction. Conjugates of this nature can be formed by mixing a solution of the polysulfone polymer described herein with a solution of the elastomeric polymer.

In accordance with one aspect of the invention, the conjugates comprises a copolymer that comprises at least one block of a polysulfone polymer (A) and at least one block of an elastomeric polymer (B) in a general formula such as AB, ABA or BAB.

In one embodiment, the block copolymer has a structure of any of the following formulae:

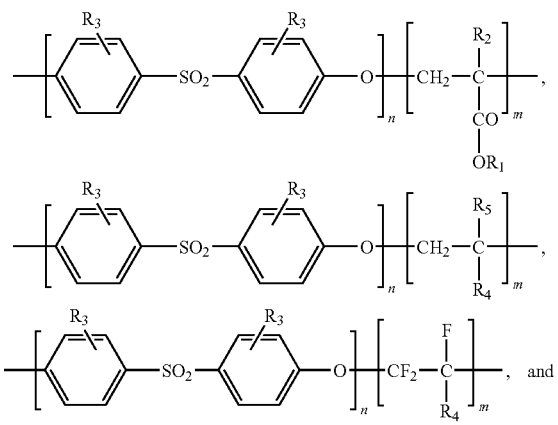

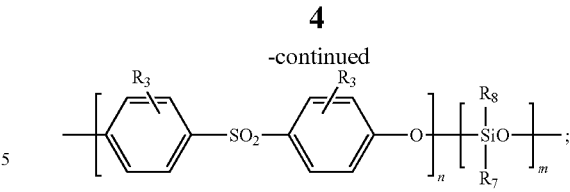

wherein $R_1$ is C1 to C10 alkyl, C2, C4 and C6 hydroxyalkyl, C1 to C6 fluoroalkyl, phenyl, substituted phenyl, polyethylene glycol, and polyalkylene oxide such as ethylene oxide or propylene oxide; wherein $R_2$, $R_4$, $R_5$, $R_7$ and $R_8$ are independently hydrogen, C1 to C6 alkyl, C2, C4 and C6 hydroxyalkyl, C1 to C6 fluoroalkyl, phenyl, substituted phenyl, carboxyl, amido, or ester groups bearing a polyethylene glycol, and polyalkylene oxide; wherein $R_3$ is hydrogen, alkyl, cycloalkyl, phenyl, carboxyl, halo, amino, hydroxyl, amido, sulfido, and polyalkylene oxide; wherein $R_9$ and $R_{10}$ are independently H, $CH_3$, F and $CF_3$; wherein $R_6$ is a perfluoroalkyl group; and wherein n and m are independently positive integers. In an example, $R_1$ is butyl, isobutyl or isopropyl; $R_2$ is hydrogen or methyl; $R_3$ is hydrogen, halo, or methyl; $R_4$ and $R_5$ are independently hydrogen, methyl, ethyl, isopropyl, butyl, isobutyl, or phenyl; $R_6$ is F, $CF_3$, $CF_2CF_3$, $CF_2CF_2CF_3$, perfluoroisopropyl, perfluorobutyl or perfluoroisobutyl; $R_7$ and $R_8$ are independently methyl, ethyl, propyl, isopropyl, butyl, or isobutyl group. In another example, $R_1$ is butyl; $R_2$ is methyl; $R_3$ is hydrogen; $R_4$ and $R_5$ are methyl groups; $R_6$ is $CF_3$; and $R_7$ and $R_8$ are methyl group. In a further example, the copolymer has one of the following structures:

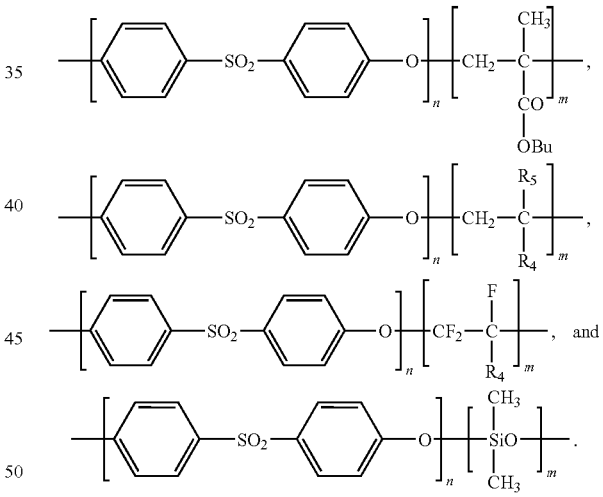

The copolymers described herein can be formed by linking the polysulfone block and the elastomeric block by chemical reaction. Generally, block copolymers described herein can be formed by (1) attaching a functional group to either the polysulfone or elastomeric polymer or both, and (2) forming the block copolymer by linking the polysulfone and the elastomeric polymer via the functional group. For example, where the polysulfone is a polyether sulfone block copolymer, it can be synthesized by a variety of techniques via the formation of a polymer graft, the formation of a pseudo-living free-radical polymer by ATRP (atom-transfer radical polymerization), reverse-ATRP (see, for example, Qin, et al., J. Polym Sci. Part A, Polym Chem. 39:3464-3473 (2001)), thermal (see, for example, Liu, et al., J. Macromol. Sci-Pure Appl. Chem. A38(2):209-219 (2001)) or photo-initiator (see, for example, Otsu, et al., Makromolek Chem. Rapid Commun. 3:127 (1982)) using a macro-initiator, or the formation of appropriate reactive functionalities with anionic polymerizations. For example, hydrophilic components such as methacrylic acid, hydroxyl ethyl methacrylate, etc. can be introduced into the copolymer by polymerizing one of the hydrophilic components with a useful monomer such as a long chain methacrylate.

Schemes I-IV illustrate some exemplary methods of making the copolymer comprising at least a block of the polysulfone polymer and at least a second block of an elastomeric polymer. Scheme I shows the synthesis of a tolyl endcapped macromer of methacrylate ($M_w$: 10,000 to 100,000 Daltons):

Scheme I

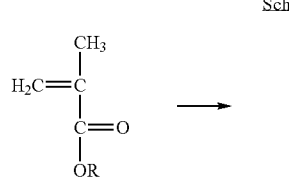

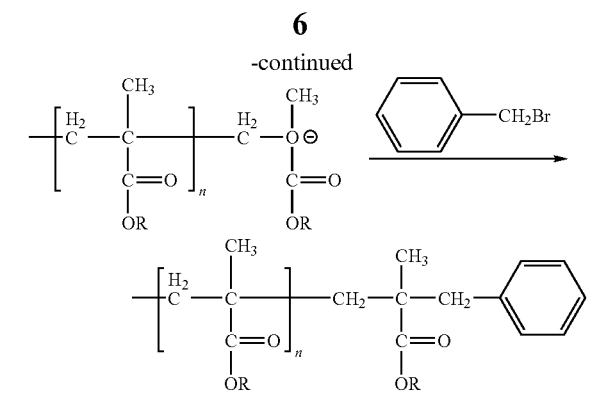

As shown in Scheme I, a methacrylate can be first subjected to polymerization with an initiator, for example, an anionic initiator. The polymerization can be then terminated with a material having a desired functionality, for example, tolyl halide with a phenyl ring, forming a macromer of methacrylate endcapped with the desired functionality. The tolyl-endcapped-methacrylate macromer can then be used to terminate the Friedels Craft condensation reaction of an aromatic compound such as phenol ether or bibenzene with the acrylate tolyl functionality (Scheme II):

Scheme II

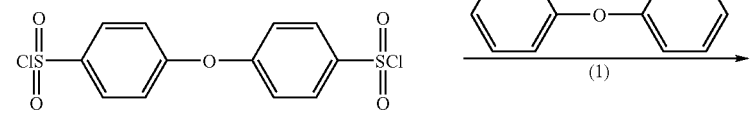

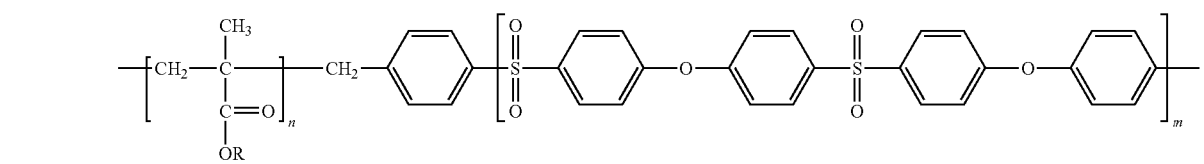

Alternatively, the copolymer can be synthesized via the formation of a macromer of polysulfone followed by the formation of the block of an elastomeric polymer (Schemes III-IV). In Scheme III, the Friedels Craft condensation reaction of an aromatic compound such as phenol ether or bibenzene is terminated with toluene, forming a toluene endcapped macromer of sulfone. The toluene is further derivatized to form a macro-initiator of a polysulfone macromer.

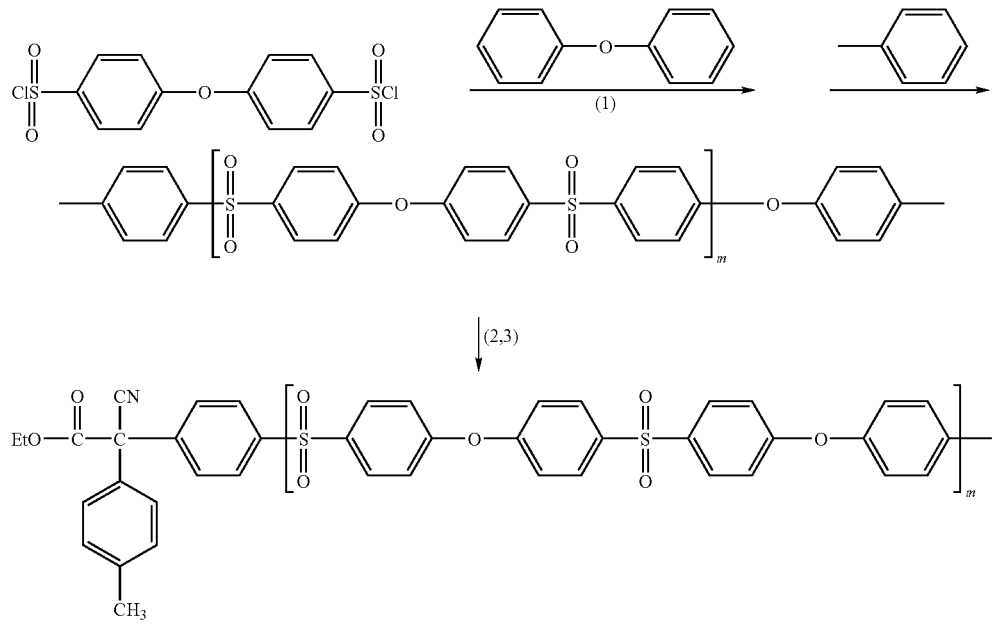

The macro-initiator of polysulfone macromer can then be used to initiate the polymerization of acrylate or methacrylate under thermal conditions, for example, heating at about 80° C. in the presence of a base such as $(CH_3)_3COK$ in a solvent such as tetrahydrofuran (THF) to generate the block copolymer, poly(ether sulfone-block-acrylate) or poly(ether sulfone-block-methacrylate) (Scheme IV).

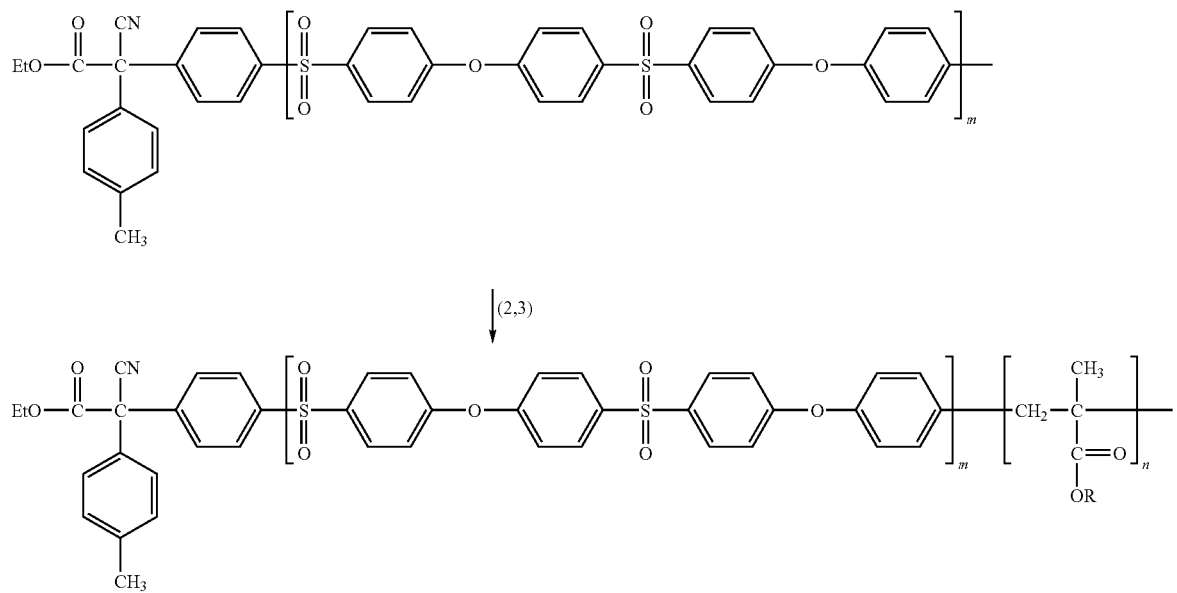

The block copolymer of polysulfone and an elastomeric polymer can be synthesized via other routes and techniques documented in the field (see, for example, Hadjichristidis, et al., Block Copolymers: Synthetic Strategies, Physical Properties, and Applications, Wiley Europe (2002)).

Bioactive Agents

The bioactive agent can be any agent which is biologically active, for example, a therapeutic, prophylactic, or diagnostic agent. Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules which bind to complementary DNA to inhibit transcription, and ribozymes. Compounds with a wide range of molecular weight can be used, for example, between 100 and 500,000 grams or more per mole. Examples of suitable materials include proteins such as antibodies, receptor ligands, and enzymes, peptides such as adhesion peptides, saccharides and polysaccharides, synthetic organic or inorganic drugs, and nucleic acids. Examples of materials which can be encapsulated include enzymes, blood clotting factors, inhibitors or clot dissolving agents such as streptokinase and tissue plasminogen activator; antigens for immunization; hormones and growth factors; polysaccharides such as heparin; oligonucleotides such as antisense oligonucleotides and ribozymes and retroviral vectors for use in gene therapy. Representative diagnostic agents are agents detectable by x-ray, fluorescence, magnetic resonance imaging, radioactivity, ultrasound, computer tomography (CT) and positron emission tomography (PET). Ultrasound diagnostic agents are typically a gas such as air, oxygen or perfluorocarbons.

In the case of controlled release, a wide range of different bioactive agents can be incorporated into a controlled release device. These include hydrophobic, hydrophilic, and high molecular weight macromolecules such as proteins. The bioactive compound can be incorporated into the polymeric coating in a percent loading of between 0.01% and 70% by weight, more preferably between 5% and 30% by weight.

In one embodiment, the bioactive agent can be for inhibiting the activity of vascular smooth muscle cells. More specifically, the bioactive agent can be aimed at inhibiting abnormal or inappropriate migration and/or proliferation of smooth muscle cells for the inhibition of restenosis. The bioactive agent can also include any substance capable of exerting a therapeutic or prophylactic effect in the practice of the present invention. For example, the bioactive agent can be for enhancing wound healing in a vascular site or improving the structural and elastic properties of the vascular site. Examples of active agents include antiproliferative substances such as actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin $I_1$, actinomycin $X_1$, and actinomycin $C_1$. The bioactive agent can also fall under the genus of antineoplastic, anti-inflammatory, antiplatelet, anticoagulant, antifibrin, antithrombin, antimitotic, antibiotic, antiallergic and antioxidant substances. Examples of such antineoplastics and/or antimitotics include paclitaxel (e.g. TAXOL® by Bristol-Myers Squibb Co., Stamford, Conn.), docetaxel (e.g. Taxotere®, from Aventis S.A., Frankfurt, Germany) methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax ä (Biogen, Inc., Cambridge, Mass.). Examples of such cytostatic or antiproliferative agents include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon, genetically engineered epithelial cells, tacrolimus, dexamethasone, rapamycin, Everolimus, 40-O-(3-hydroxy)propyl-rapamycin, 40-O-[2-(2-hydroxy)ethoxy]ethyl-rapamycin, and 40-O-tetrazole-rapamycin. The foregoing substances are listed by way of example and are not meant to be limiting. Other active agents which are currently available or that may be developed in the future are equally applicable.

The dosage or concentration of the bioactive agent required to produce a favorable therapeutic effect should be less than the level at which the bioactive agent produces toxic effects and greater than the level at which non-therapeutic results are obtained. The dosage or concentration of the bioactive agent required to inhibit the desired cellular activity of the vascular region can depend upon factors such as the particular circumstances of the patient; the nature of the trauma; the nature of the therapy desired; the time over which the ingredient administered resides at the vascular site; and if other active agents are employed, the nature and type of the substance or combination of substances. Therapeutic effective dosages can be determined empirically, for example by infusing vessels from suitable animal model systems and using immunohistochemical, to determine the biological effect of a particular dose curve as established by pharmokinetic and pharmodynamic studies. Standard pharmacological test procedures to determine dosages are understood by one of ordinary skill in the art.

Methods of Using the Polysulfone Composition

The polysulfone composition can be coated onto any implantable device by any established coating process, e.g., a spray process. Generally, the coating process involves dissolving or suspending the composition in a solvent to form a solution or a suspension of the coating composition, and then applying the solution or suspension to an implantable device such as a DES.

As used herein, an implantable device may be any suitable medical substrate that can be implanted in a human or veterinary patient. A preferred implantable device is DES. Examples of stents include self-expandable stents, balloon-expandable stents, and stent-grafts. Other exemplary implantable devices include grafts (e.g., aortic grafts), artificial heart valves, cerebrospinal fluid shunts, pacemaker electrodes, and endocardial leads (e.g., FINELINE and ENDOTAK, available from Guidant Corporation, Santa Clara, Calif.). The underlying structure of the device can be of virtually any design. The device can be made of a metallic material or an alloy such as, but not limited to, cobalt chromium alloy (ELGILOY), stainless steel (316L), high nitrogen stainless steel, e.g., BIODUR 108, cobalt chrome alloy L-605, "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable or biostable polymers could also be used with the embodiments of the present invention.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method of forming an implantable device, comprising forming a coating on the implantable device, the coating comprising a polymeric composition comprising a block copolymer comprising a polysulfone (A) and an elastomeric polymer (B), wherein the polysulfone and the elastomeric polymer form a conjugate by direct chemical bonding, and
wherein the elastomeric polymer is selected from the group consisting of polyisobutylene, polyperfluoroalkylene, polyhexafluoropentene, poly(butyl methacrylate), poly(lauryl methacrylate), polyalkylene oxide, polyalkylene oxide acrylate, and a combination thereof.

2. The method of claim 1, wherein the elastomeric polymer is selected from the group consisting of polyisobutylene, polyperfluoroalkylene, polyhexafluoropentene, poly(butyl methacrylate), poly(lauryl methacrylate), polyalkylene oxide acrylate, and a combination thereof.

3. The method of claim 1, wherein the block copolymer comprises at least one block of a polysulfone polymer (A) and at least one block of an elastomeric polymer (B) in a general formula selected from AB, ABA or BAB.

4. The method of claim 1 wherein the implantable device is a stent.

5. The method of claim 1, wherein the coating further comprises a bioactive agent.

6. The method of claim 5, wherein the bioactive agent is selected from the group consisting of tacrolimus, dexamethasone, rapamycin, Everolimus, 40-O-(3-hydroxy)propyl-rapamycin, 40-O-[2-(2-hydroxy)ethoxy]ethyl-rapamycin, and 40-O-tetrazole-rapamycin, sirolimus, sirolimus derivatives, paclitaxel, taxoids, estradiol, steroidal anti-inflammatory agents, antibiotics, nitric oxide donors, super oxide dismutases, super oxide dismutase mimics, 4-amino-2,2,6,6-tetramethylpiperidine-1-oxyl (4-amino-TEMPO), and a combination thereof.

7. The method of claim 1, wherein the polysulfone and the elastomeric polymer form a conjugate comprising a block copolymer, wherein the block copolymer is selected from the group consisting of

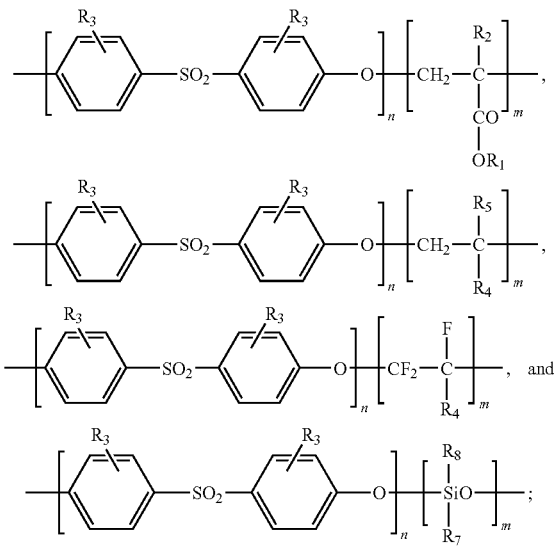

wherein $R_1$ is selected from the group consisting of C1 to C10 alkyl, C2, C4 and C6 hydroxyalkyl, C1 to C6 fluoroalkyl, phenyl, substituted phenyl, polyethylene glycol, polyalkylene oxide, ethylene oxide and propylene oxide;

wherein $R_2$, $R_4$, $R_5$, $R_7$ and $R_8$ are independently selected from the group consisting of hydrogen, C1 to C6 alkyl, C2, C4 and C6 hydroxyalkyl, C1 to C6 fluoroalkyl, phenyl, substituted phenyl, carboxyl, amido, ester groups bearing a polyethylene glycol, and polyalkylene oxide;

wherein $R_3$ is selected from the group consisting of hydrogen, alkyl, cycloalkyl, phenyl, carboxyl, halo, amino, hydroxyl, amido, sulfido, and polyalkylene oxide;

wherein $R_6$ is a perfluoroalkyl group;

wherein $R_4$, $R_5$, and $R_6$ are selected such that the

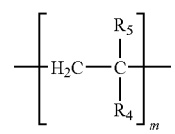

block and the

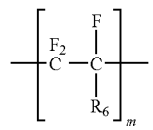

are elastomeric; and wherein n and m are independently positive integers.

8. The method of claim 7, wherein $R_1$ is butyl, isobutyl or isopropyl;

wherein $R_2$ is hydrogen or methyl;

wherein $R_3$ is hydrogen, halo, or methyl;

wherein $R_4$ and $R_5$ are independently hydrogen, methyl, ethyl, isopropyl, butyl, isobutyl, or phenyl;

wherein $R_6$ is $CF_2CF_3$, $CF_2CF_2CF_3$, perfluoroisopropyl, perfluorobutyl or perfluoroisobutyl; and wherein $R_7$ and $R_8$ are independently methyl, ethyl, propyl, isopropyl, butyl, or isobutyl group.

9. The method of claim 7, wherein $R_1$ is butyl;

wherein $R_2$ is methyl;

wherein $R_3$ is hydrogen;

wherein $R_4$ or $R_5$ are methyl groups; and wherein $R_7$ and $R_8$ are methyl groups.

* * * * *